United States Patent [19]
Otsubo et al.

[11] Patent Number: 5,941,865
[45] Date of Patent: Aug. 24, 1999

[54] DISPOSABLE ABSORBENT GARMENT OF PANTS TYPE

[75] Inventors: Toshifumi Otsubo, Ehime-ken; Hiroyuki Soga, Kagawa-ken, both of Japan

[73] Assignee: Uni-Charm Corporation, Ehime-ken, Japan

[21] Appl. No.: 08/851,462

[22] Filed: May 5, 1997

[30] Foreign Application Priority Data

May 7, 1996 [JP] Japan .................................... 8-112590

[51] Int. Cl.[6] ........................................................ A61F 13/15
[52] U.S. Cl. ...................... 604/385.2; 604/378; 604/396
[58] Field of Search ............................ 604/385.1, 385.2, 604/393–396, 378–380; 2/400–406

[56] References Cited

U.S. PATENT DOCUMENTS

| 3,848,598 | 11/1974 | Mesek | 604/379 |
|---|---|---|---|
| 4,624,666 | 11/1986 | DeRussett et al. | 604/379 |
| 4,692,163 | 9/1987 | Widlund et al. | 604/385.2 |
| 4,820,295 | 4/1989 | Chapas et al. | 604/379 |
| 5,366,452 | 11/1994 | Widlund et al. | 604/385.2 |
| 5,449,353 | 9/1995 | Watanabe et al. | 604/385.2 |

FOREIGN PATENT DOCUMENTS

| 4-166150 | 6/1992 | Japan . | |
| 4-289201 | 10/1992 | Japan . | |
| 4354948 | 12/1992 | Japan | 604/394 |
| 4371147 | 12/1992 | Japan | 604/385.2 |
| 4371148 | 12/1992 | Japan | 604/385.2 |
| 2082643 | 3/1982 | United Kingdom | 604/379 |
| 9317648 | 9/1993 | WIPO | 604/394 |

OTHER PUBLICATIONS

Translation of JP 4371148, Nov. 1997.
Translation of JP 437147, Nov. 1997.

*Primary Examiner*—John G. Weiss
*Assistant Examiner*—K. M. Reichle
*Attorney, Agent, or Firm*—Lowe Hauptman; Gopstein Gilman & Berner

[57] ABSTRACT

A pull-on disposable absorbent garment such as a diaper has a front waist region, a rear waist region and a crotch region defined by a topsheet, a backsheet and an absorbent core disposed therebetween. The front and rear waist regions are provided with a plurality of elastic members arranged most densely in proximity of longitudinal opposite ends of the absorbent core.

2 Claims, 2 Drawing Sheets

DISPOSABLE ABSORBENT GARMENT OF PANTS TYPE

BACKGROUND OF THE INVENTION

The present invention relates generally to a pull-on disposable absorbent garment such as a pants type disposable diaper, training pants, incontinence pants or the like.

Pull-on disposable absorbent garments are well known in which a waist-opening and a pair of leg-openings are provided with elastic members to provide edges of these openings with stretchability. Elastic members are also provided between a waist-opening edge and crotch region of the absorbent garment so that a liquid-absorbent core is maintained in tight contact with the wearer's skin under pressure exerted by the elastic members from an outer surface of the absorbent core. This type of garment is disclosed, for example, by Japanese Patent Application Laid-Open Publication Nos. Hei4-166150 and Hei4-289201.

However, when the location is elastically maintained in close contact with the wearer's skin to prevent leakage of body fluids, there is created a feeling of discomfort against the wearer's waist or stomach due to the elastic members.

The present invention is based on the finding that leakage of body fluids can be prevented by improving fitness of the garment not over the entire extent of the absorbent core but only along at least a portion of a peripheral edge of the absorbent core and thereby improve comfort.

SUMMARY OF THE INVENTION

In view of the above problem, it is a principal object of the invention to improve fitness of the garment to the wearer's body at least in the proximity of longitudinally opposite ends of the absorbent core.

The object set forth above is achieved, according to the invention, by on a pull-on disposable absorbent garment comprising a laminate of a liquid-absorbent core having longitudinally opposite ends and transversely opposite side edges, a liquid-permeable topsheet and a liquid-impermeable backsheet. The two sheets respectively cover opposite surfaces of the absorbent core and extend beyond the longitudinally opposite ends as well as beyond transversely opposite side edges of the absorbent core. The laminate has a front waist region, a rear waist region and a crotch region extending between said front and rear waist regions. With the laminate longitudinally folded in two sections, the front and rear waist regions are bonded to each other along transversely opposite side edges of the respective regions to define a waist-opening and a pair of leg-openings. The front and rear waist regions inclusive of the waist-opening as well as the pair of leg-openings are provided with a plurality of elastic members extending circumferentially of these openings and longitudinally spaced apart one from another.

The pull-on disposable absorbent garment, in accordance with one embodiment, comprises the front waist region including a first waist subregion defined by an area extending no greater than 20 mm above a front end of the absorbent core and an area extending no more than 20 mm below the front end of the absorbent core and a second waist subregion defined between the first waist subregion and an upper edge of the leg opening. Each waist subregion includes a plurality of said elastic members extending therein, wherein the elastic members arranged in the first waist subregion are made of a material and have cross-sectional areas which are substantially uniform with cross-sectional areas of and a material making the elastic members of the second waist subregion. Adjacent ones of the elastic members in the first waist subregion are spaced apart from each other a distance which is dimensioned to be smaller than the distance adjacent ones of the elastic members in the second waist subregion are spaced apart from each other. Each elastic member in the first waist subregion has an elongation stress lower than an elongation stress of each elastic member in the second waist subregion. The aforementioned elongation stresses in the first and second waist subregions are further achieved by requiring each of the elastic members in the first waist subregion to have an elongation ratio smaller than each of the elastic members in the second waist subregion.

According to a further aspect of the invention, within a region of the absorbent core extending rearward from said front end by at least 10 mm as measured in a longitudinal direction thereof, the absorbent core has a thickness gradually decreasing toward the front end.

The pull-on disposable absorbent garment of the invention allows the garment to be reliably maintained in tight contact with the wearer's skin in proximity of the longitudinally opposite ends of the absorbent core and thereby prevents discharged body fluids from leaking beyond these ends of the absorbent core without degrading comfort.

This is because the elastic members are more densely arranged in proximity of the longitudinally opposite ends of the absorbent core than in the remaining regions. Furthermore, the garment according to the invention provides a good appearance when worn since the thickness of the absorbent core in proximity of the longitudinally opposite ends thereof is dimensioned to be gradually decreased toward the ends and thereby a difference in level between the absorbent core and the wearer's skin is minimized.

DESCRIPTION OF THE PREFERRED EMBODIMENT

Details of a pull-on disposable absorbent garment according to the invention will be better understood from the following description of a pull-on disposable diaper as a typical embodiment of the invention and with reference to the accompanying drawings.

Figure 1:
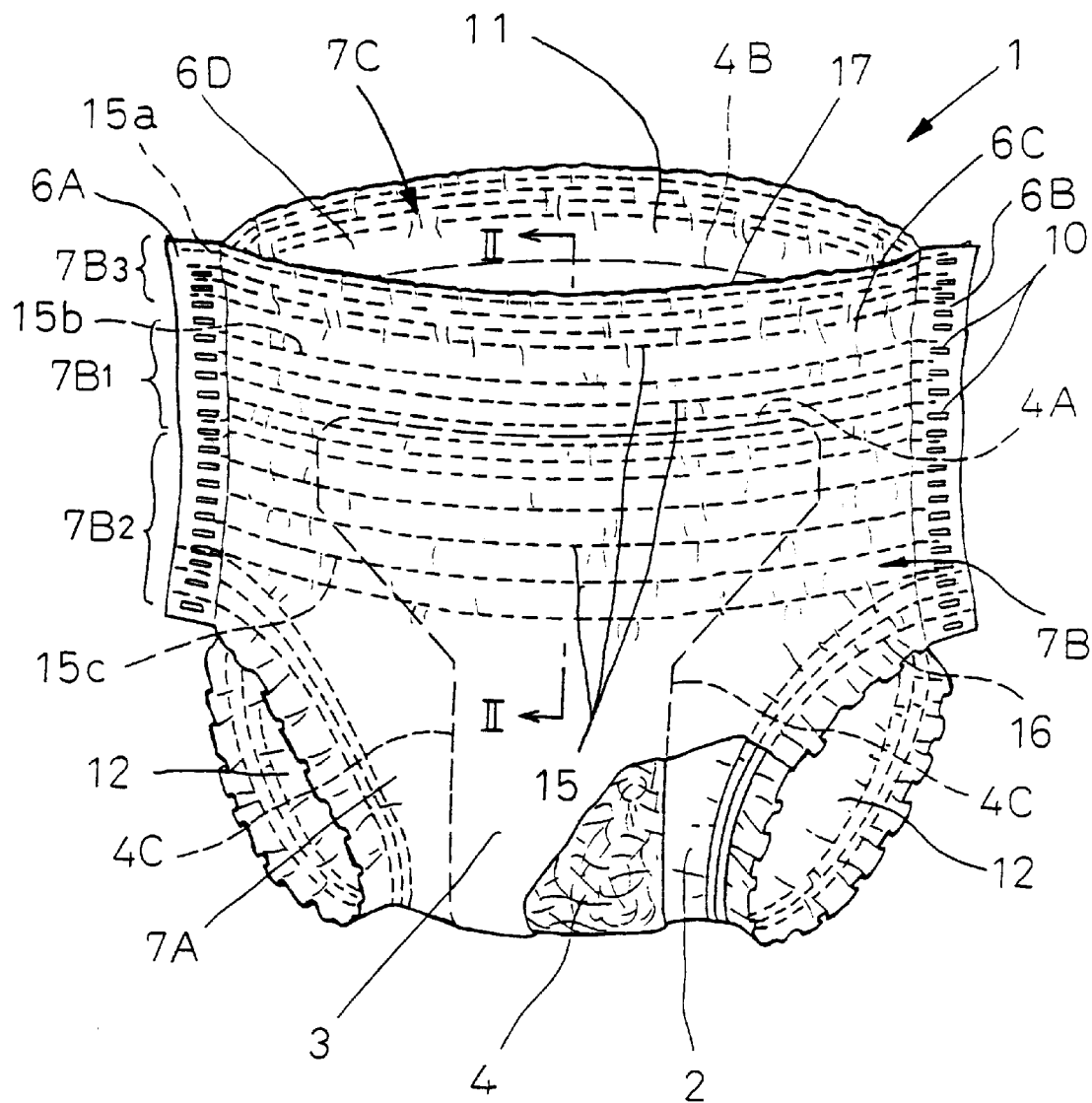
FIG. 1 is a perspective view of a pull-on disposable diaper according to the invention as partially broken away.

Referring to FIG. 1, a pull-on disposable diaper comprises a laminate 1 including a liquid-permeable topsheet 2, a liquid-impermeable backsheet 3 and a liquid-absorbent core 4 disposed therebetween. The absorbent core 4 is hourglass- or I-shaped and has a peripheral edge longitudinally defined by front and rear ends 4A, 4B and transversely defined by opposite side edges 4C, 4C. The topsheet 2 and backsheet 3 are dimensioned to extend outward beyond the peripheral edges of the absorbent core 4 and are bonded to each other along portions thereof extending outward beyond the core peripheral edges so as to form transversely opposite side flaps 6A, 6B and longitudinally opposite end flaps 6C, 6D. Laminate 1 can be divided into front and rear waist regions 7B, 7C with a relatively narrow crotch region 7A extending substantially in the middle between the front and rear waist regions 7B, 7C. The laminate 1 is longitudinally folded at the crotch region 7A in two sections with the topsheet 2 inside. The front and rear waist regions 7B, 7C are bonded to each other along transversely opposite side edges thereof by bonding means 10 provided along these side edges so as to define a waist-opening 11 and a pair of leg-openings 12. The front waist region 7B inclusive of the waist-opening 11 and the pair of leg-openings 12 are respectively proved with circumferentially stretchable elastic members 15a, 15b, 15c; and 16.

Figure 2:
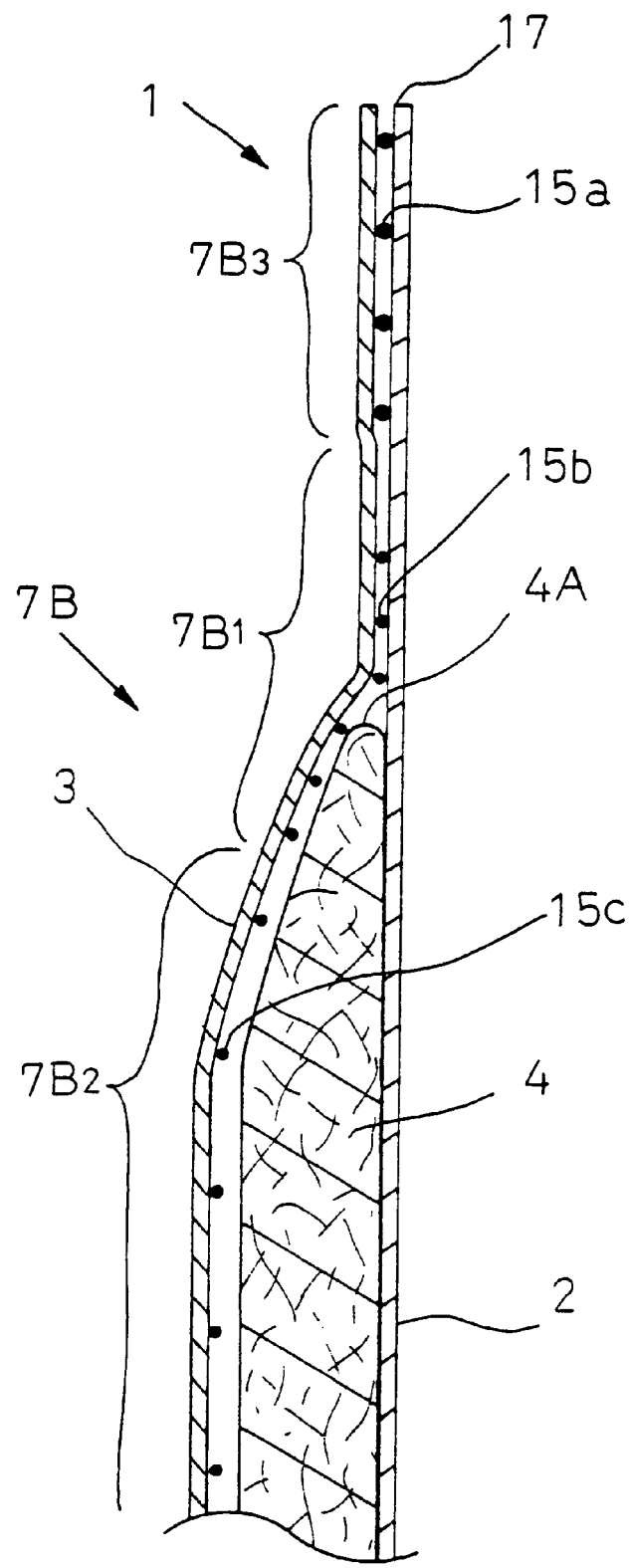
FIG. 2 is a sectional view taken along line II—II in FIG. 1.

Referring to FIG. 2, a portion of the absorbent core 4 occupying the front waist region 7B is configured so that, within a region of the absorbent core 4 including a front end 4A and extending rearward from the front end 4A by at least 10 mm as measured in its longitudinal direction, the absorbent core 4 may have a thickness gradually decreasing toward the front end 4A. Such configuration may be obtained by gradually decreasing a quantity of the absorbent core forming material in this region toward the front end 4A or by appropriately compressing the absorbent core forming material in this region. The portions of the topsheet 2 and backsheet 3 extending outward from the front end 4A are bonded to each other to form a waist-opening edge 17. Though not shown, it should be understood that the rear waist region 7C is also constructed in the same manner as the front waist region 7B.

The front waist region 7B is composed of a first waist subregion $7B_1$ defined by each 20 mm in maximum above and below the front end 4A of the absorbent core 4, a second waist subregion $7B_2$ defined between the first waist subregion $7B_1$ and an upper edge of the leg-opening 12, and a third waist subregion $7B_3$ defined between the first waist subregion $7B_1$ and the waist-opening edge 17. These waist subregions $7B_1$, $7B_2$, $7B_3$ are respectively provided with a plurality of elastic members 15a, 15b, 15c extending in circumferential directions thereof and spaced apart one from another in a vertical direction thereof. The elastic members 15a, 15b, 15c are secured to an inner surface of the topsheet 2 or respective inner surfaces of the topsheet 2 and backsheet 3 in elastically extended conditions thereof. Each of the elastic members 15a provided in the third waist subregion $7B_3$ has a cross-sectional area and an elongation stress larger and higher than each of the elastic members 15b, 15c, provided in the first and second waist subregions $7B_1$, $7B_2$. Each of the elastic members 15b, 15c provided in the first and second waist subregions $7B_1$, $7B_2$ is substantially uniform in terms of cross-sectional area and elongation stress. The distance by which each pair of adjacent elastic members 15b are spaced apart from each other in the first waist subregion $7B_1$ is dimensioned to be smaller than the distance by which each pair of adjacent elastic members 15c are spaced apart from each other in the second waist subregion $7B_2$ so that a surface pressure per unit area is larger in the first waist subregion $7B_1$ than in the second waist subregion $7B_2$. The elastic members 15b, 15c, 15a are provided in the respective waist subregions $7B_1$, $7B_2$, $7B_3$ with a 50% elongation stress of 5–50 g/150 mm and an elongation ratio of 1.1–2.5.

With the arrangement in which a surface pressure per unit area is higher in the first waist subregion $7B_1$ than in the second waist subregion $7B_2$ as described above, the portion of the first waist subregion $7B_1$ extending above and below the front end 4A of the absorbent core 4 is maintained in contact with the wearer's skin not withstanding the rigidity of the absorbent core 4 during use of the diaper. In other words, the first waist subregion $7B_1$ is advantageously maintained in contact with the wearer's skin more tightly than the second waist subregion $7B_2$. However, such locally higher surface pressure will give the wearer a feeling of discomfort.

To eliminate this problem, the first and second waist subregions $7B_1$, $7B_2$ are preferably substantially the same with respect to the surface pressure per unit area but with the former providing a better fitness than the latter. This is achieved by spacing each pair of adjacent elastic members 15b in the first waist subregion $7B_1$ a distance from each other which is less than the distance in which each pair of adjacent elastic members 15c are spaced apart from each other in the second waist subregion $7B_2$; in addition, each of the elastic members 15b in the first waist subregion $7B_1$ has an elongation stress appropriately lower than each of the elastic members 15c in the second waist subregion $7B_2$. Such adjustment of the elongation stress is achieved by an arrangement that each of the elastic members 15b in the first waist subregion $7B_1$ has an elongation ratio smaller than each of the elastic members 15c in the second waist subregion $7B_2$ while the elastic members 15b, 15c in the first and second waist subregions $7B_1$, $7B_2$, respectively, are substantially uniform as far as a material as well as a cross-sectional area are concerned or an arrangement that each of the elastic members 15b in the first waist subregion $7B_1$ has a cross-sectional area appropriately smaller than each of the elastic members 15c in the second waist subregion $7B2$ while the elastic members 15b, 15c in the first and second waist subregions $7B_1$, $7B_2$ are substantially uniform as far as a material as well as an elongation ratio are concerned.

While the cross-sections of the elastic members 15 may be either circular or rectangular, this cross-section is preferably dimensioned to have a diameter as measured in a direction of this width larger than a diameter as measured in a direction of this thickness.

While the description has been given above with respect to the front waist region 7B, it should be understood that the rear waist region 7C may have an arrangement similar to or more or less different from the arrangement of the front waist region 7B.

The diaper of the arrangement as has been described hereinabove reliably prevents discharged body fluids from leaking beyond the front end 4A of the absorbent core 4, since the elastic members 15 are densely arranged in the region just above and below the front end 4A of the absorbent core 4 which is reliably maintained in contact with the wearer's skin in proximity of the front end 4A. The elastic members 15a provided in the third waist subregion $7B_3$ extend along the waist line of the front and rear waist regions 7B, 7C substantially without a break.

It is possible to improve fitness in the proximity of the front end 4A of the absorbent core by replacing the elastic members 15b with one or more relatively wide band-like elastic member(s) in the first waist subregion $7B_1$. In this case, the band-like elastic member should have a moisture permeability sufficient to assure breathability essential to the diaper.

For implementation of the invention a nonwoven fabric or a perforated plastic film may be employed as the topsheet 2 and a plastic film such as a polyethylene film may be employed as the backsheet 3. Fluff pulp or a mixture of fluff pulp and a hydrocolloid material such as superabsorbent polymer particles formed in a desired shape by the well known technique may be employed as the absorbent core 4. A suitable material having a rubber elasticity such as rubber or plastic elastomer may be employed as the elastic members 15, 16.

What is claimed is:

1. A pull-on disposable absorbent garment comprising a laminate of a liquid-absorbent core having longitudinally opposite ends and transversely opposite side edges, a liquid-permeable topsheet and a liquid-impermeable backsheet, said topsheet and said backsheet respectively covering opposite surfaces of said absorbent core and extending both beyond said longitudinally opposite ends and said transversely opposite side edges of said absorbent core, said laminate further having a front waist region, a rear waist region and a crotch region extending between said front and rear waist regions, wherein said front and rear waist regions are bonded to each other along transversely opposite side edges of the respective regions to define a waist-opening and a pair of leg-openings, said front and rear waist regions inclusive of said waist-opening as well as said pair of leg-openings including a plurality of elastic members extending circumferentially of these openings and longitudinally spaced apart one from another, at least said front waist region including a first waist subregion defined by an area extending no greater than 20 mm above a front end of said absorbent core and an area extending no more than 20 mm below the front end of said absorbent core and a second waist subregion defined between said first waist subregion and an upper edge of said leg-opening, each waist subregion including a plurality of said elastic members extending therein wherein the elastic members arranged in said first waist subregion are made of a material and have cross-sectional areas which are substantially uniform with cross-sectional areas of and a material making the elastic members of the second waist subregion, and adjacent ones of said elastic members in said first waist subregion are spaced apart from each other a distance which is dimensioned to be smaller than a distance adjacent ones of said elastic members in said second waist subregion are spaced apart from each other; and wherein each elastic member in said first waist subregion has an elongation stress lower than an elongation stress of each elastic member in said second waist subregion, wherein the respective elongation stress are achieved by an arrangement such that each of the elastic members in said first waist subregion has an elongation ratio smaller than each of the elastic members in said second waist subregion.

2. The garment according to claim 1, wherein, within a region of said absorbent core extending longitudinally rearward at least 10 mm from said front end, said absorbent core has a thickness gradually decreasing toward said front end.

* * * * *